(12) United States Patent
Dicarlo et al.

(10) Patent No.: US 8,043,361 B2
(45) Date of Patent: Oct. 25, 2011

(54) IMPLANTABLE MEDICAL DEVICES, AND METHODS OF DELIVERING THE SAME

(75) Inventors: Paul Dicarlo, Middleboro, MA (US); Ilya Yampolsky, West Roxbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1003 days.

(21) Appl. No.: 11/010,129

(22) Filed: Dec. 10, 2004

(65) Prior Publication Data
US 2006/0129232 A1    Jun. 15, 2006

(51) Int. Cl.
*A61F 2/82* (2006.01)

(52) U.S. Cl. .................. 623/1.18; 623/1.15; 623/1.3

(58) Field of Classification Search .................. 623/1.18, 623/1.19, 1.3, 1.15; *A61F 2/06*
See application file for complete search history.

(56) References Cited

U.S. PATENT DOCUMENTS

| | | |
|---|---|---|
| 3,383,336 A | 5/1968 | Kuyama et al. |
| 3,459,725 A | 8/1969 | Natta et al. |
| 3,563,973 A | 2/1971 | Arditti et al. |
| 4,080,357 A | 3/1978 | Gergen et al. |
| 4,503,569 A | 3/1985 | Dotter |
| 4,531,933 A | 7/1985 | Norton et al. |
| 4,612,241 A | 9/1986 | Howard, Jr. |
| 4,893,623 A | 1/1990 | Rosenbluth |
| 4,969,890 A | 11/1990 | Sugita et al. |
| 4,990,155 A | 2/1991 | Wilkoff |
| 5,007,926 A | 4/1991 | Derbyshire |
| 5,037,427 A | 8/1991 | Harada et al. |
| 5,062,829 A | 11/1991 | Pryor et al. |
| 5,064,435 A | 11/1991 | Porter |
| 5,089,005 A | 2/1992 | Harada |
| 5,100,429 A | 3/1992 | Sinofsky et al. |
| 5,145,935 A | 9/1992 | Hayashi |
| 5,147,385 A | 9/1992 | Beck et al. |
| 5,163,952 A | 11/1992 | Froix |
| 5,189,110 A | 2/1993 | Ikematu et al. |
| 5,258,020 A | 11/1993 | Froix |
| 5,282,854 A | 2/1994 | Yagi et al. |
| 5,395,882 A | 3/1995 | Siol et al. |
| 5,421,955 A | 6/1995 | Lau et al. |

(Continued)

FOREIGN PATENT DOCUMENTS

DE    102 28 120 A1    1/2004
(Continued)

OTHER PUBLICATIONS

Sarbu et al., "Synthesis of Hydroxy-Telechelic Poly(methyl acrylate) and Polystyrene by Atom Transfer Radical Coupling", Macromolecules, 37, pp. 9694-9700, 2004.

(Continued)

*Primary Examiner* — Thomas J Sweet
*Assistant Examiner* — Jason-Dennis Stewart
(74) *Attorney, Agent, or Firm* — Mayer & Williams PC; David B. Bonham; Keum J. Park

(57) ABSTRACT

A tubular endoprosthesis including a polymeric material is disclosed. The endoprosthesis has a collapsed position that can be reverted to a first expanded position larger than the collapsed position by heating to a first temperature subsequent to insertion of the endoprosthesis into a cavity or lumen in a mammal. The endoprosthesis can be further expanded to a second expanded position within the cavity or lumen.

42 Claims, 6 Drawing Sheets

U.S. PATENT DOCUMENTS

| | | | |
|---|---|---|---|
| 5,466,242 A | 11/1995 | Mori | |
| 5,496,311 A | 3/1996 | Abele et al. | |
| 5,506,300 A | 4/1996 | Ward et al. | |
| 5,601,593 A * | 2/1997 | Freitag | 623/1.19 |
| 5,603,722 A | 2/1997 | Phan et al. | |
| 5,607,467 A | 3/1997 | Froix | |
| 5,645,559 A | 7/1997 | Hachtman et al. | |
| 5,665,822 A | 9/1997 | Bitler et al. | |
| 5,674,241 A | 10/1997 | Bley et al. | |
| 5,674,242 A | 10/1997 | Phan et al. | |
| 5,716,410 A * | 2/1998 | Wang et al. | 606/191 |
| 5,741,333 A | 4/1998 | Frid | |
| 5,755,769 A | 5/1998 | Richard et al. | |
| 5,769,883 A | 6/1998 | Buscemi et al. | |
| 5,776,162 A | 7/1998 | Kleshinksi | |
| 5,800,516 A | 9/1998 | Fine et al. | |
| 5,830,179 A | 11/1998 | Mikus et al. | |
| 5,849,037 A | 12/1998 | Frid | |
| 5,876,432 A | 3/1999 | Lau et al. | |
| 5,880,240 A | 3/1999 | Tsuno | |
| 5,889,118 A | 3/1999 | Delgado et al. | |
| 5,908,918 A | 6/1999 | Chen et al. | |
| 5,910,357 A | 6/1999 | Hachisuka et al. | |
| 5,928,217 A | 7/1999 | Mikus et al. | |
| 5,955,559 A | 9/1999 | Handlin, Jr. et al. | |
| 5,964,744 A | 10/1999 | Balbierz et al. | |
| 5,968,070 A | 10/1999 | Bley et al. | |
| 5,997,563 A | 12/1999 | Kretzers | |
| 6,024,764 A | 2/2000 | Schroeppel | |
| 6,033,413 A | 3/2000 | Mikus et al. | |
| 6,086,204 A | 7/2000 | Magnante | |
| 6,086,610 A | 7/2000 | Duerig et al. | |
| 6,099,533 A | 8/2000 | Shah | |
| 6,139,536 A | 10/2000 | Mikus et al. | |
| 6,156,842 A | 12/2000 | Hoenig et al. | |
| 6,160,084 A | 12/2000 | Langer et al. | |
| 6,174,305 B1 | 1/2001 | Mikus et al. | |
| 6,179,878 B1 | 1/2001 | Duerig et al. | |
| 6,217,609 B1 | 4/2001 | Haverkost | |
| 6,241,691 B1 | 6/2001 | Ferrera et al. | |
| 6,248,129 B1 | 6/2001 | Froix | |
| 6,283,992 B1 | 9/2001 | Hankh et al. | |
| 6,287,326 B1 | 9/2001 | Pecor | |
| 6,315,791 B1 | 11/2001 | Gingras et al. | |
| 6,323,459 B1 | 11/2001 | Maynard | |
| 6,348,065 B1 | 2/2002 | Brown et al. | |
| 6,364,904 B1 | 4/2002 | Smith | |
| 6,368,346 B1 | 4/2002 | Jadhav | |
| 6,388,043 B1 | 5/2002 | Langer et al. | |
| 6,395,038 B1 | 5/2002 | Schroeppel | |
| 6,413,273 B1 | 7/2002 | Baum et al. | |
| 6,416,545 B1 | 7/2002 | Mikus et al. | |
| 6,478,773 B1 | 11/2002 | Gandhi et al. | |
| 6,485,507 B1 | 11/2002 | Walak et al. | |
| 6,517,569 B2 | 2/2003 | Mikus et al. | |
| 6,517,570 B1 | 2/2003 | Lau et al. | |
| 6,530,950 B1 | 3/2003 | Alvarado et al. | |
| 6,538,089 B1 | 3/2003 | Samra et al. | |
| 6,679,605 B2 | 1/2004 | Zhou et al. | |
| 6,720,402 B2 | 4/2004 | Langer et al. | |
| 6,852,825 B2 | 2/2005 | Lendlein et al. | |
| 2001/0029398 A1 | 10/2001 | Jadhav | |
| 2002/0007222 A1 | 1/2002 | Desai | |
| 2002/0015519 A1 | 2/2002 | Tokas et al. | |
| 2002/0055787 A1 | 5/2002 | Lennox et al. | |
| 2002/0128706 A1 | 9/2002 | Osypka | |
| 2002/0151967 A1 | 10/2002 | Mikus et al. | |
| 2002/0156523 A1 | 10/2002 | Lau et al. | |
| 2002/0198584 A1 | 12/2002 | Unsworth et al. | |
| 2003/0033003 A1 * | 2/2003 | Harrison et al. | 623/1.15 |
| 2003/0040803 A1 | 2/2003 | Rioux et al. | |
| 2003/0045923 A1 | 3/2003 | Bashiri | |
| 2003/0055198 A1 | 3/2003 | Langer et al. | |
| 2003/0060530 A1 | 3/2003 | Topolkaraev et al. | |
| 2003/0060793 A1 | 3/2003 | Topolkaraev et al. | |
| 2003/0074052 A1 * | 4/2003 | Besselink | 623/1.15 |
| 2003/0191276 A1 | 10/2003 | Lendlein et al. | |
| 2004/0014929 A1 | 1/2004 | Lendlein et al. | |
| 2004/0015187 A1 | 1/2004 | Lendlein et al. | |
| 2004/0015261 A1 | 1/2004 | Hoffman et al. | |
| 2004/0024143 A1 | 2/2004 | Lendlein et al. | |
| 2005/0010275 A1 | 1/2005 | Sahatjian et al. | |
| 2005/0216074 A1 | 9/2005 | Sahatjian et al. | |
| 2006/0287710 A1 * | 12/2006 | Lendlein et al. | 623/1.19 |

FOREIGN PATENT DOCUMENTS

| | | |
|---|---|---|
| EP | 0 277 816 A1 | 8/1988 |
| EP | 0 324 946 A2 | 7/1989 |
| EP | 0 343 442 A2 | 11/1989 |
| EP | 0 368 274 A2 | 5/1990 |
| EP | 0 385 443 A2 | 9/1990 |
| EP | 0 422 693 B1 | 6/1995 |
| EP | 1 000 958 A2 | 5/2000 |
| EP | 0 100 958 A2 | 7/2003 |
| JP | 612301051 | 10/1986 |
| JP | 62192440 | 8/1987 |
| JP | 63145325 | 6/1988 |
| JP | 2274526 | 8/1990 |
| JP | 2232212 | 9/1990 |
| JP | 2255830 | 10/1990 |
| JP | 2258817 | 10/1990 |
| JP | 3068610 | 3/1991 |
| JP | 3068611 | 3/1991 |
| JP | 4100831 | 4/1992 |
| JP | 8301952 | 11/1996 |
| JP | 9235329 | 9/1997 |
| JP | 11-154420 | 8/1999 |
| JP | 11302493 | 11/1999 |
| JP | 2000319423 | 11/2000 |
| WO | WO 94/14890 | 7/1994 |
| WO | WO 95/26762 | 10/1995 |
| WO | WO 97/46633 | 12/1997 |
| WO | WO 98/25544 | 6/1998 |
| WO | WO 99/42147 | 8/1999 |
| WO | WO 99/42528 | 8/1999 |
| WO | WO 99/42548 | 8/1999 |
| WO | WO 00/10485 | 3/2000 |
| WO | WO 00/33770 | 6/2000 |
| WO | WO 00/46262 | 8/2000 |
| WO | WO 00/71554 A2 | 11/2000 |
| WO | WO 00/78246 A2 | 12/2000 |
| WO | WO 01/07499 A1 | 2/2001 |
| WO | WO 01/56641 A1 | 8/2001 |
| WO | WO 01/80936 A1 | 11/2001 |
| WO | WO 01/91822 A1 | 12/2001 |
| WO | WO 02/39875 A2 | 5/2002 |
| WO | WO 02/083786 A1 | 10/2002 |
| WO | WO 01/93783 A2 | 12/2002 |
| WO | WO 03/015663 A1 | 2/2003 |
| WO | WO 2004/015840 A2 | 2/2003 |
| WO | WO 03/035743 A1 | 5/2003 |
| WO | WO 03/084490 A1 | 10/2003 |
| WO | WO 03/084491 A1 | 10/2003 |
| WO | WO 03/088818 A2 | 10/2003 |
| WO | WO 2004/006885 A2 | 1/2004 |
| WO | WO 2004/032799 A2 | 4/2004 |
| WO | WO 2004/033515 A2 | 4/2004 |
| WO | WO 2004/033539 A1 | 4/2004 |
| WO | WO 2004/033553 A1 | 4/2004 |
| WO | WO 2004/073690 A1 | 9/2004 |
| WO | WO 2004/110515 A1 | 12/2004 |
| WO | WO 2005/009523 A1 | 2/2005 |
| WO | WO 2005/070988 A1 | 8/2005 |

OTHER PUBLICATIONS

"Hydroxyl Terminated Polybutadiene Resins and Derivtives—Poly bd® and Krasol®", Sartomer Product Bulletin, Sep. 2004.

Zhu et al., "Shape-Memory Effects of Radiation Crosslinked Poly($\epsilon$-caprolactone)", Journal of Applied Polymer Science, vol. 90, pp. 1589-1595, 2003.

Rousseau et al., "Shape Memory Effect Exhibited by Smectic-C Liquid Crystalline Elastomers" J. Am. Chem. Soc., 125, pp. 15300-15301, 2003.

Gupta et al., "Effect of solvent exposure on the Properties of hyroxy-terminated polybutadiene-based polyurethanes", Polym. Int. 52, pp. 938-948, 2003.

Liu et al., "Shape Memory of Hydrogen-Bonded Polymer Network/ Poly(ethylene glycol) Complexes", Chengdu Institute of Organic Chemistry, Chinese Academy of Sciences, 2003.

Ge et al., "Synthesis of Thermoplastic Polyurethanes Bearing Nanostructured Hard Segments: New Shape Memory Polymers" Polymer Program, Institute of Materials Science and Department of Engineering, UCONN, (Abstract, 2 pp.), Jul. 2003.

Lendlein et al., "Biodegradable, Elastic Shape-Memory Polymers for Potential Biomedical Applications", Science, vol. 296, May 31, 2002.

Liu, et al., "Chemically Cross-Linked Polycylooctene: Synthesis, Characterization and Shape Memory Behavior" Macromolecules, 35, pp. 9868-9874, 2002.

Dinger, et al., "High Turnover Numbers with Ruthenium-Based Metathesis Catalysts" Advanced Synthesis Catalysis, vol. 344, pp. 671-677, 2002.

Lendlein et al., "Shape-Memory Polymers", Angew. Chem. Int. Ed. 41, pp. 2034-2057, 2002.

Chun et al., "Enhanced Dynamic Mechanical and Shape-Memory Properties of a Poly(ethyleneterephthalate)-Poly(ethylene glycol) Copolymer Crosslinked by Maleic Anhydride", Journal of Applied Polymer Science, vol. 83, pp. 27-37, 2002.

Lendlein et al., "AB-Polymer Networks Based on Oligo(ε-caprolactone) Segments Showing Shape-Memory Properties" Proc. Natl. Acad. Sci., USA, 98(3), pp. 842-847, 2001.

Jeong et al., "Miscibility and Shape Memory Property of Poly(vinyl chloride)/Thermoplastic Polyurethane Blends", Journal of Materials Science, 36, pp. 5457-5463, 2001.

Jeong et al., "Miscibility and Shape Memory Effect of Thermoplastic Polyurethane Blends with Phenoxy Resin", European Polymer Journal, 37, pp. 2245-2252, 2001.

Van Humbeeck, "Shape Memory Alloys: A Material and a Technology", Advanced Engineering Materials, vol. 3, No. 11, pp. 837-850, 2001.

Fu et al., "Structural Development During Deformation of Polyurethane Containing Polyhedral Oligomeric Silsesquioxanes (POSS) Molecules", Polymer 42, pp. 599-611, 2001.

Boochathum et al., "Vulcanization of Cis- and Trans-Polyisoprene and Their Blends: Cure Characteristics and Crosslink Distribution", European Polymer Journal 37, pp. 417-427, 2001.

Boochathum et al., Vulcanization of Cis- and Trans-Polyisoprene and Their Blends: Crystallization Characteristics and Properties, European Polymer Journal, 37, pp. 429-434, 2001.

"Silsesquioxanes, Bridging the Gap Between Polymers & Ceramics" ChemFiles vol. 1, No. 6, 2001.

Bielawski et al., "Highly efficient syntheses of acetoxy- and hyroxy-terminated telechelic poly(butadiene)s using ruthenium catalysts containing N-heterocyclic ligands", Polymer, 42, pp. 4939-4945, 2001.

Mather et al., "Strain Recovery in Drawn POSS Hybrid Thermoplastics," XIIIth International Congress on Rheology, Cambridge, UK, 4, pp. 53-55, 2000.

Mather et al., "Strain Recovery in POSS Hybrid Thermoplastics," Polymer Preprints 41(1), pp. 528-529, 2000.

Jeon et al., "Shape Memory and Nanostructure in Poly(norbornyl-POSS) Copolymers", Polymer International, 49, pp. 453-457, 2000.

Fu et al., "Nanoscale Reinforcement of Polyhedral Oligomeric Silsesquioxane (POSS) in Polyurethane Elastomer", Polymer Int. 49, pp. 437-440, 2000.

Bielawski et al., "Highly Efficient Ring-Opening Metathesis Polymerization (ROMP) Using New Ruthenium Catalysts Containing N-Heterocyclic Carbene Ligands", Angew. Chem. Int. Ed., 39, No. 16, pp. 2903-2906, 2000.

Reyntjens et al., "Polymer Networks Containing Crystallizable Poly(octadecyl vinyl ether) Segments for Shape-Memory Materials", Macromol. Rapid. Commun., 20(5), pp. 251-255, 1999.

Du Prez et al., "Segmented Networks by Cationic Polymerization: Design and Applications" NATO Sci. Ser., Ser. E, pp. 75-98, 1999.

Ramanathan et al., "Polyurethane", Polymer Data Handbook, pp. 870-873, 1999.

Ramanathan et al., "Polyurethane elastomers", Polymer Data Handbook, pp. 874-877, 1999.

Ramanathan et al., "Polyurethane urea", Polymer Data Handbook, pp. 878-881, 1999.

Kaneko et al., "Shape Memory Gels with Multi-Stimuli-Responses", Proc. SPIE-Int. Soc. Opt. Eng., 3669, pp. 199-208, 1999.

Lin et al., "Study on Shape-Memory Behavior of Polyether-Based Polyurethanes. II. Influence of Soft-Segment Molecular Weight", Journal of Applied Polymer Science, vol. 69, pp. 1575-1586, 1998.

Lin et al., "Study on Shape-Memory Behavior of Polyether-Based Polyurethanes. I. Influence of the Hard-Segment Content", Journal of Applied Polymer Science, vol. 69, pp. 1563-1574, 1998.

Kim et al., "Polyurethane Ionomers Having Shape Memory Effects", Polymer, vol. 39, No. 13, pp. 2803-2808, 1998.

Wei et al., "Shape-Memory Materials and Hybrid Composites for Smart Systems", Journal of Materials Science 33, pp. 3743-3762, 1998.

Goethals et al. "Poly(Vinyl Ethers) as Building Blocks for New Materials" Macromol. Symp., 132, pp. 57-64, 1998.

Mauler et al., "Liquid-crystalline polyacrylate crosslinked with α, ω polyisoprene diacrylate segments", Polymer Bulletin, 41, pp. 291-297, 1998.

Irie, Shape Memory Polymers, Cambridge University Press: Cambridge, UK, pp. 203-219, 1998.

Paul Starck, "Dynamic Mechanical Thermal Analysis on Ziegler-Natta and Metallocene Type Ethylene Copolymers", Eur. Poly. J. vol. 33, No. 3, pp. 339-348, 1997.

Gajria et al., "Miscibility and Biodegradability of Blends of Poly(Lactic Acid) and Poly(Vinyl Acetate)", Polymer, vol. 37, pp. 437-444, 1996.

Sung et al., "Properties of Segmented Poly(urethaneureas) Based on 2,4-Toluene Diisocyanate. 1. Thermal Transitions, X-ray Studies, and Comparison with Segmented Poly(urethanes)", Macromolecules, 13, pp. 111-116, 1980.

Kagami et al., "Shape Memory Behaviors of Crosslinked Copolymers Containing Stearyl Acrylate" Macromol. Rapid. Commun., 17(8), pp. 539-543, 1996.

Schwab et al., "Synthesis and Applications of RuC12(=CHR')(PR3)2: The Influence of the Alkylidene Moiety on Metathesis Activity", J. Am. Chem. Soc., 118, pp. 100-110, 1996.

Mauler et al., "Functional Group Determination in Hydroxilated Polymer", Eur. Polym. J., vol. 31, No. 1, pp. 51-55, 1995.

Nakayama, K., "Properties and Applications of Shape-Memory Polymers", International Polymer Science and Technology, 18, T/43-48, 1991.

Schneider et al., "Crystallinity of trans-Polyoctenamer: Characterization and Influence of Sample History", Journal of Molecular Catalysis, 46, pp. 395-403, 1988.

Yeh et al., "Radiation-Induced Crosslinking: Effect on Structure of Polyethylene", Colloid & Polymer Sci. 263, pp. 109-115, 1985.

Oh et al., "Dynamic Mechanical Properties of Carbon Black Filled Trans-polyoctenamer Vulcanizates", Abstract Only, (Oct. 19, 1985).

Bassi et al., "The Triclinic Structure of trans-Polyoctenamer", European Polymer Journal, vol. 4, pp. 123-132, 1968.

Bassi et al., "The Monoclinic Structure of Even Trans-Polyalkenamers", European Polymer Journal, vol. 3, pp. 339-352, 1967.

Calderon et al., "Melting Temperature of trans-Polyoctenamer", Journal of Polymer Science: Part A-2, vol. 5, pp. 1283-1292, 1967.

Kannan et al., "Polyhedral Oligomeric Silsesquixoane Nanocomposites: The Next Generation Material for Biomedical Applications", Acc. Chem. Res., vol. 38, No. 11, pp. 879-884, 2005.

Fu et al., "Structural Development during deformation of polyurethane containing polyhedral oligomeric silsesquioxanes (POSS) molecules", Polymer, 42, pp. 599-611, 2001.

Fan et al., "Synthesis and Properties of Polyurethane Modified with Aminoethylaminopropyl Poly(dimethyl siloxane)", Journal of Applied Polymer Science, vol. 74, pp. 2552-2558, 1999.

Schwabb et al., "Polyhedral Oligomeric Sil silsesquixoanes (POSS): Silicon Based Monomers and Their Use in the Preparation of Hybrid Polyurethanes", Mat. Res. Soc. Symp. Proc., vol. 519, pp. 21-27, 1998.

Sahatjian et al., "Implantable Medical Devices", U.S. Appl. No. 10/958,435, filed Oct. 5, 2004.

Wache, et al., "Development of a polymer stent with shape memory effect as a drug delivery system", Journal of Materials Science: Materials in Medicine, 14, 109-112, (2003).

Lendlein et al., "Biodegradable, Elastic Shape-Memory Polymers for Potential Biomedical Applications", Science, vol. 296, pp. 1673-1676, May 31, 2002.

Valimaa et al., "Viscoelastic memory and self-expansion of self-reinforced bioabsorbable stents", Biomaterials, 23, pp. 3575-3582, 2002.

"Suite of Shape-Memory Polymers", Chemical & Engineering, Feb. 5, 2001.

Woojin Lee, "Polymer Gel Based Actuator: Dynamic model of gel for real time control", Massachuetts Institute of Technology, Department of Mechanical Engineering, May 3, 1996.

Brochure, Degussa High Performance Polymers, The Rubber with Unique Properties, Vestenamer©, Undated.

* cited by examiner

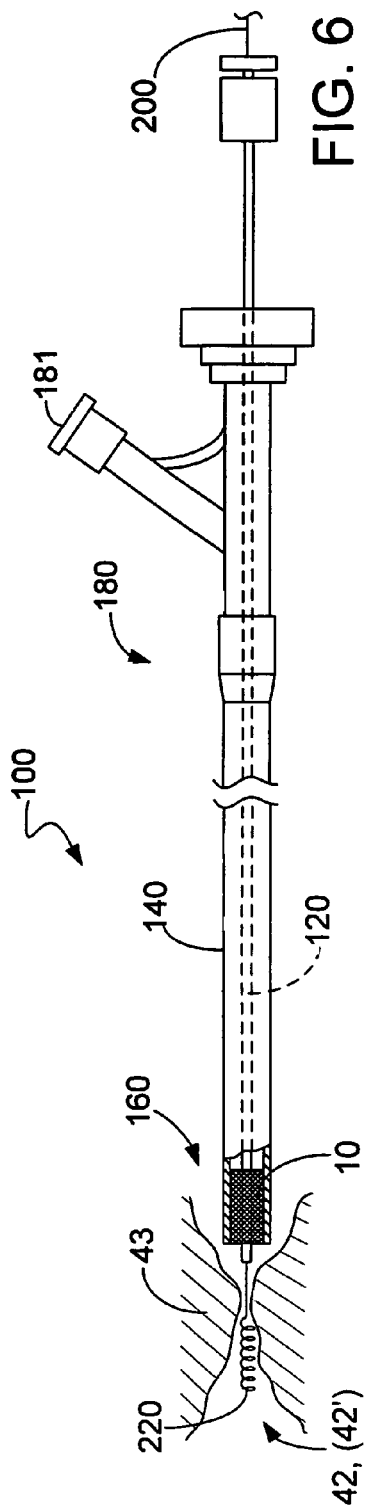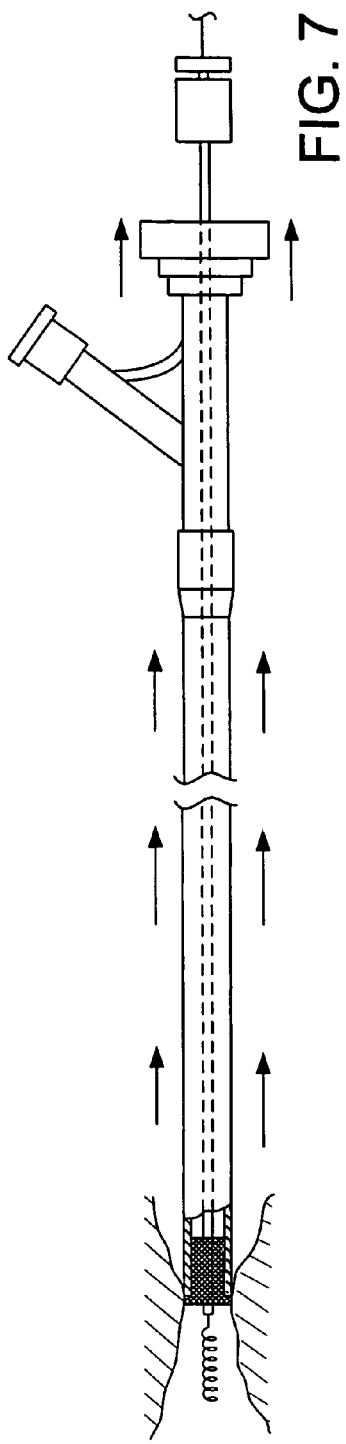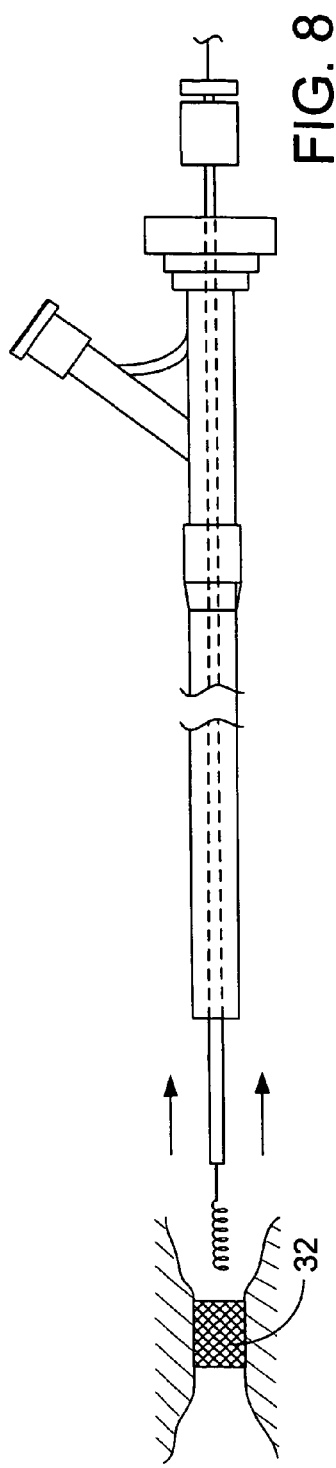

IMPLANTABLE MEDICAL DEVICES, AND METHODS OF DELIVERING THE SAME

TECHNICAL FIELD

This invention relates to implantable medical devices, and methods of delivering the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

In some cases, passageways can become re-occluded, a phenomenon often called "restenosis." After restenosis, often another endoprosthesis is deployed within the first endoprosthesis to re-open the passageway.

SUMMARY

This invention relates to implantable medical devices, and methods of delivering the same.

Generally, an endoprosthesis is described that can be deployed into a cavity or lumen in a collapsed position, and then reverted to a first expanded position larger than the collapsed position to support the cavity or lumen. At a later time, e.g., after restenosis of the cavity or lumen, the endoprosthesis can be further expanded.

In one aspect, the invention features a tubular endoprosthesis, e.g., a stent, that includes a polymeric material. The endoprosthesis has at least one longitudinal element embedded in a wall of the endoprosthesis. The endoprosthesis has a collapsed position that can be reverted to a first expanded position larger than the collapsed position by heating to a first temperature subsequent to insertion of the endoprosthesis into a cavity or lumen, e.g., a vascular or a non-vascular lumen, in a mammal. The endoprosthesis can be further expanded from the first expanded position to a second expanded position within the cavity or lumen by heating to a second temperature higher than the first temperature.

In some embodiments, the endoprosthesis is substantially circular in transverse cross-section.

In some embodiments, the longitudinal element includes a metal, e.g., stainless steel. Longitudinal elements can be, e.g., monofilaments and/or multifilament. In embodiments in which the longitudinal elements are monofilaments, the monofilaments can have a circular transverse cross-section, e.g., having a diameter of from about 0.0005 inch to about 0.010 inch. The endoprosthesis can include, e.g., from about two to about twelve longitudinal elements. In some implementations, the longitudinal element extends substantially along an entire longitudinal length of the endoprosthesis.

In some embodiments, the wall includes an aperture or many apertures. The aperture or apertures can be, e.g., circular in transverse cross-section. In some implementations, the longitudinal elements are disposed longitudinally across apertures.

In some embodiments, the tubular endoprosthesis includes a coating that includes a therapeutic agent. In some embodiments, the coating is on an outer surface of the endoprosthesis. In specific embodiments, the coating is an outer surface of the endoprosthesis, and the therapeutic agent also is dispersed generally throughout the polymeric material. The therapeutic agent can be chosen, e.g., to prevent restenosis. For example, the therapeutic agent can be paclitaxel. The polymeric material can also include a radio-opaque agent and/or a thermal conductor, e.g., boron nitride.

In some embodiments, the polymeric material includes a natural polymer, e.g., zein, casein, gelatin, gluten, serum albumin, collagen, polysaccharides, polyhyaluronic acid, poly(3-hydroxyalkanoate)s, alginate, dextran, cellulose, collagen or mixtures of these polymers. In some implementations, the polymeric material includes a synthetic polymer, e.g., chemical derivatives of collagen, chemical derivatives of cellulose, polyphosphazenes, poly(vinyl alcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyesters, degradable polymers, polyester amides, polyanhydrides, polycarbonates, polyorthoesters, polylactides, polyglycolides, polysiloxanes, polyurethanes, cellulose derivatives or mixtures of these polymers. In some embodiments, polymeric material includes mixtures of natural and synthetic polymers. In some embodiments, the polymeric material is cross-linked.

In specific embodiments, the tubular endoprosthesis has a collapsed transverse dimension and a collapsed longitudinal length, both measured at the collapsed position. The first expanded position has a first expanded transverse dimension that is at least fifty percent larger than the collapsed transverse dimension and a first expanded longitudinal length that is at least fifty percent of the collapsed longitudinal length.

In other specific embodiments, the endoprosthesis has a first expanded transverse dimension and a first expanded longitudinal length, both measured at the first expanded position. The second expanded position has a second expanded transverse dimension that is at least twenty-five percent larger than the first expanded transverse dimension and a second expanded longitudinal length that is at least fifty percent of the first expanded longitudinal length.

In another aspect, the invention features a method of treating a cavity or lumen in a mammal. The method includes inserting, into the cavity or lumen in the mammal, a tubular endoprosthesis that includes a polymeric material. The endoprosthesis has at least one longitudinal element embedded in a wall of the endoprosthesis and has a collapsed position that can be reverted to a first expanded position larger than the collapsed position by heating to a first temperature subsequent to insertion of the endoprosthesis into a cavity or lumen in a mammal. The endoprosthesis can be further expanded from the first expanded position to a second expanded position within the cavity or lumen in the mammal by heating to a second temperature higher than the first temperature. The inserted endoprosthesis is heated to the first temperature to revert the collapsed position to the first expanded position.

In some embodiments, the method further includes heating the inserted endoprosthesis to the second temperature to further expand the endoprosthesis to the second expanded position. The heating can be performed, e.g., with a liquid. For example, heating can be performed by a delivery tube, e.g., a balloon catheter, that includes a warmed liquid.

In some embodiments, the first temperature is, e.g., from about 37° C. to about 55° C. and the second temperature is, e.g., from about 40° C. to about 75° C.

In some embodiments, the lumen is a vascular lumen.

In another aspect, the invention features a method of treating a cavity or lumen in a mammal. The method include inserting, into the cavity or lumen in the mammal, a tubular endoprosthesis that includes a polymeric material. The endoprosthesis has a collapsed position that can be reverted to a first expanded position larger than the collapsed position by heating to a first temperature subsequent to insertion of the endoprosthesis into a cavity or lumen in a mammal. The endoprosthesis can be further expanded from the first expanded position to a second expanded position within the cavity or lumen in the mammal by heating to a second temperature higher than the first temperature. The inserted endoprosthesis is heated to the first temperature to revert the collapsed position to the first expanded position, and then the inserted endoprosthesis is heated to the second temperature to further expand the endoprosthesis to the second expanded position.

In another aspect, the invention features an endoprosthesis that includes a polymeric material having at least one longitudinal element embedded in a wall of the endoprosthesis.

In some embodiments, the endoprosthesis includes from about two to twelve longitudinal elements.

Embodiments may have one or more of the following advantages. The endoprotheses described herein can be deployed into a cavity or lumen in a collapsed position, and then reverted to a first expanded position larger than the collapsed position to support the cavity or lumen. At a later time, e.g., after restenosis of the cavity or lumen, the endoprosthesis can be further expanded, often without the need for secondary angioplasty. In some implementations, the endoprosthesis can be further expanded from outside the body. Many of the embodiments also show a reduced foreshortening and improved radio-opacity which can, e.g., improve placement of the endoprosthesis within a cavity or lumen.

The details of one or more embodiments of the invention are set forth in the accompanying drawings and the description below. Other features, and advantages of the invention will be apparent from the description and drawings and from the claims.

DESCRIPTION OF DRAWINGS

FIGS. 6-8 are mixed views of an endoprosthesis delivery system, the views being side views away from an occlusion, and cross-sectional proximate the occlusion.

DETAILED DESCRIPTION

Figure 1:
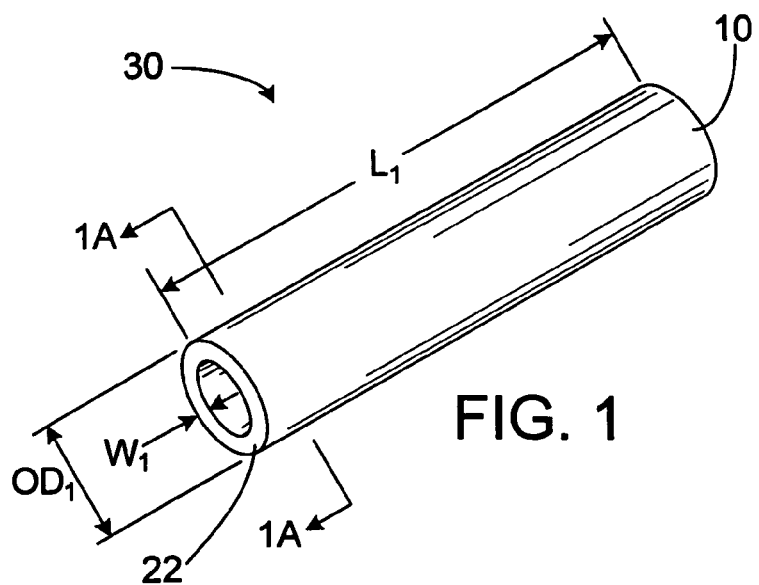
FIG. 1 is a perspective view of an endoprosthesis in a collapsed position.
Figure 1A:
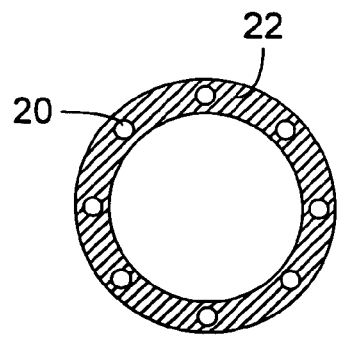
FIG. 1A is a cross-sectional view of the endoprosthesis shown in FIG. 1, taken along 1A-1A.

Generally, an endoprosthesis is described herein that can be deployed into a cavity or lumen of a mammal in a collapsed position at onset of stenosis, and then reverted to a first expanded position larger than the collapsed position to support an occluded cavity or lumen. After onset of restenosis, the endoprosthesis can be further expanded to a second expanded position larger than the first expanded position within the cavity or lumen to further support the cavity or lumen.

Referring to FIGS. 1-5, an elongated, circular transverse cross-section tubular endoprosthesis 10, e.g., a stent, includes a polymeric material and has eight longitudinal elements 20 embedded in a wall 22. Endoprosthesis 10 has a collapsed position 30 that can be reverted to a first expanded position 32 larger than the collapsed position 30 by heating to a first temperature subsequent to insertion of endoprosthesis 10 into a cavity 42 or lumen 42' in a mammal, e.g., a human. Endoprosthesis 10 can be further expanded to a second expanded position 36 larger than the first expanded position 32 within the cavity 42 or lumen 42' by heating to a second temperature higher than the first temperature.

Longitudinal elements 20 can reduce endoprosthesis foreshortening during expansion from collapsed position 30 to first expanded position 32 or second expanded position 36. In addition, longitudinal elements 20 can serve as markers to aid in the delivery of endoprosthesis 10 when the elements include a radio-opaque material.

Referring now to FIGS. 6-8, an implantable medical endoprosthesis delivery system 100 includes an inner member 120 and an outer member 140 surrounding inner member 120. Endoprosthesis 10 is positioned between inner member 120 and outer member 140. The delivery system 100 includes a distal end 160 dimensioned for insertion into a body cavity 42 or lumen 42' (e.g., an artery of a human) and a proximal end 180 that resides outside the body of a subject, and that contains at least one port 181 and lumens for manipulation by a physician. A guide wire 200 with a blunted end 220 is inserted into a body cavity 42 or lumen 42' by, for example, making an incision in the femoral artery, and directing guide wire 200 to a constricted site 43 of cavity 42 or lumen 42' (e.g., an artery constricted with plaque) using, for example, fluoroscopy as a position aid. After guide wire 200 has reached constricted site 43 of body cavity 42 or lumen 42', inner member 120, endoprosthesis 10 in collapsed position 30, and outer member 140 are placed over the proximal end of guide wire 200. Inner member 120, endoprosthesis 10 and outer member 140 are moved distally over guide wire 200 and positioned within cavity 42 or lumen 42' so that endoprosthesis 10 is adjacent constricted site 43 of cavity 42 or lumen 42'. When ready to deploy, outer member 140 is moved proximally, exposing endoprosthesis 10.

Figure 4:
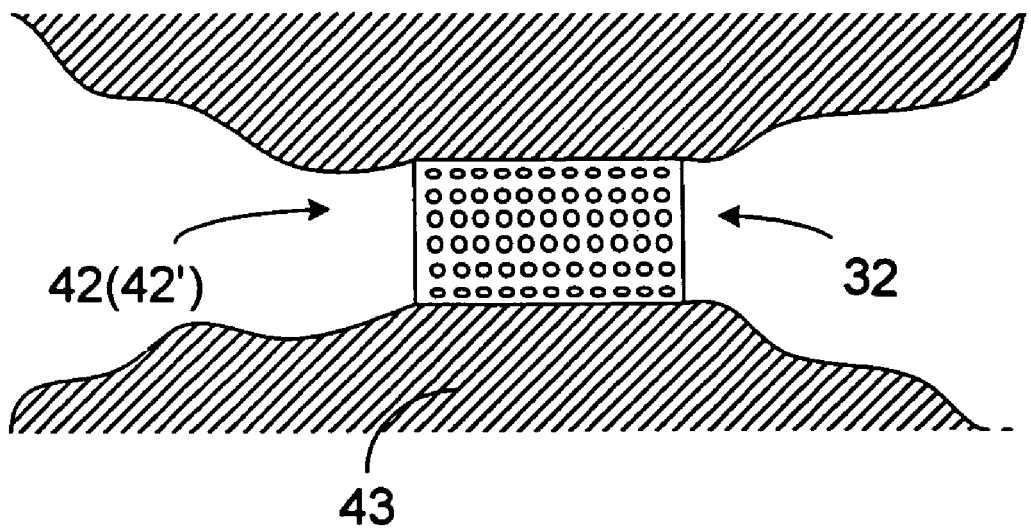
FIGS. 4 and 5 are cross-sectional views of an endoprosthesis within an occluded lumen in a first and second expanded position, respectively.
Figure 5:
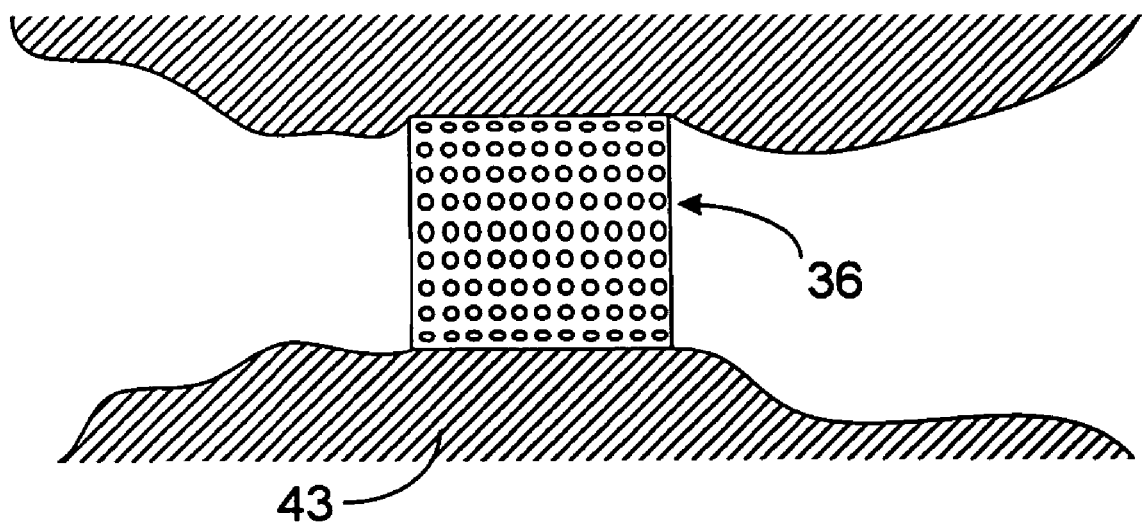

Endoprosthesis 10 having collapsed position 30 is then reverted to a first expanded position 32 larger than the collapsed position 30 by heating to a first temperature subsequent to insertion of the endoprosthesis 10 into the cavity 42 or lumen 42'. Outer member 140, inner member 120 and guide wire 200 are removed from cavity 42 or lumen 42', leaving endoprosthesis 10 in first expanded position 32 engaged with constricted site 43 (FIGS. 4 and 8). After restenosis of cavity 42 or lumen 42', endoprosthesis 10 can be further expanded to a second expanded position 36 larger than the first expanded position 32 within the cavity 42 or lumen 42' by heating to a second temperature higher than the first temperature. Further expansion to the second expanded position 36 is shown in FIG. 5. Other suitable delivery systems, methods of making delivery systems and components thereof are known. For example, those systems, methods and components described by Thompson, U.S. Pat. No. 6,623,491, Lau, U.S. Pat. No. 6,620,193, Svensson, U.S. Pat. No. 6,620,191, Euteneuer, U.S. Pat. No. 6,610,069, Fiedler, U.S. Pat. No. 6,605,109, Markling, U.S. Pat. No. 4,321,226 and Sahatjian, WO 2004032799, the contents of each of which is hereby incorporated by reference herein in its entirety.

In some implementations, heating to the first or second temperature is performed by a liquid in a tube, e.g., a balloon catheter. Heating can also be performed with radiation, e.g., infrared radiation, or radio-frequency radiation. In addition, heating can be performed using magnetic induction. In some embodiments, the first temperature is, e.g., from about 37° C. to about 55° C., and the second temperature is, e.g., 40° C. to about 75° C.

In specific implementations, heating to the second temperature is performed from outside the body of the mammal, e.g., using magnetic induction.

Longitudinal element 22 can be made of, e.g., a metal (e.g., stainless steel), a plastic (e.g., a polyamide), or a composite material. When radio-opacity is desirable, longitudinal element 22 can be radio-opaque. Longitudinal element 22 can be, e.g., in the form of a monofilament, e.g., a circular transverse cross-section monofilament that has a diameter of from about 0.0005 inch to about 0.010 inch, e.g., from about 0.001 inch to about 0.008 inch, or from about 0.002 inch to about 0.005 inch. Longitudinal element 22 can be, e.g., in the form of a multifilament, e.g., a melt-spun multifilament, having, e.g., from about 3 threads to about 250 threads, e.g., from about 5 threads to about 144 threads. The threads making up the multifilament can include a single type of material, e.g., nylon, or can include a variety of different materials, e.g., threads of nylon and stainless steel, or threads of nylon and polyester.

In some implementations, tubular endoprosthesis 10 includes from about 1 to about 50 longitudinal elements 22, e.g., from about 4 to about 30 longitudinal elements, or from about six to about 24 longitudinal elements.

In some implementations, longitudinal element(s) 22 extend(s) substantially along an entire longitudinal length of endoprosthesis 10.

Materials, e.g., polymeric materials, that can be used to make endoprosthesis 10 having a collapsed position that can be reverted to a first expanded position, and then expanded further to a second expanded position are known. Suitable polymeric materials, e.g., homopolymers, block copolymers, and blends thereof, have been described by Langer, U.S. Pat. Nos. 6,388,043 and 6,720,402, the contents of each of which is hereby incorporated by reference herein in its entirety. The polymeric materials described therein are shape memory polymers that can hold two or more shapes in memory.

In some embodiments, the polymeric material used to make endoprosthesis 10 can include a hard segment (H) and two distinct soft segments ($S_1$ and $S_2$).

In other embodiments, a polymer blend of a first multiblock copolymer and a second multiblock copolymer is utilized to make endoprosthesis 10. The first multiblock copolymer includes a hard segment ($H_1$) with a relatively high transition temperature ($T_{trans}$), e.g., glass transition temperature or melting temperature, and a soft segment ($S'_1$) with a relatively low $T_{trans}$. The second multiblock copolymer includes a different hard segment ($H_2$) with a relatively low $T_{trans}$ and the same soft segment ($S'_1$) as in the first multiblock copolymer. Since the soft segments ($S'_1$) in both the first and second multiblock copolymers are identical, the polymers are miscible in each other. The resulting blend has three transition temperatures, one for the hard segment ($H_1$) of the a first multiblock copolymer, one for hard segment ($H_2$) of the second multiblock copolymer, and one for the soft segment ($S'_1$).

Figure 2:
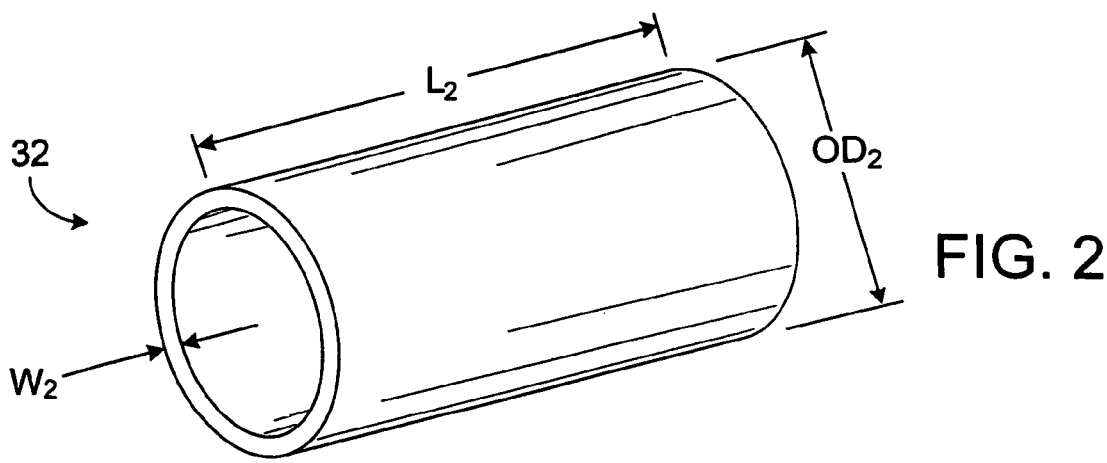
FIG. 2 is a perspective view of the endoprosthesis shown in FIG. 1 in a first expanded position.
Figure 3:
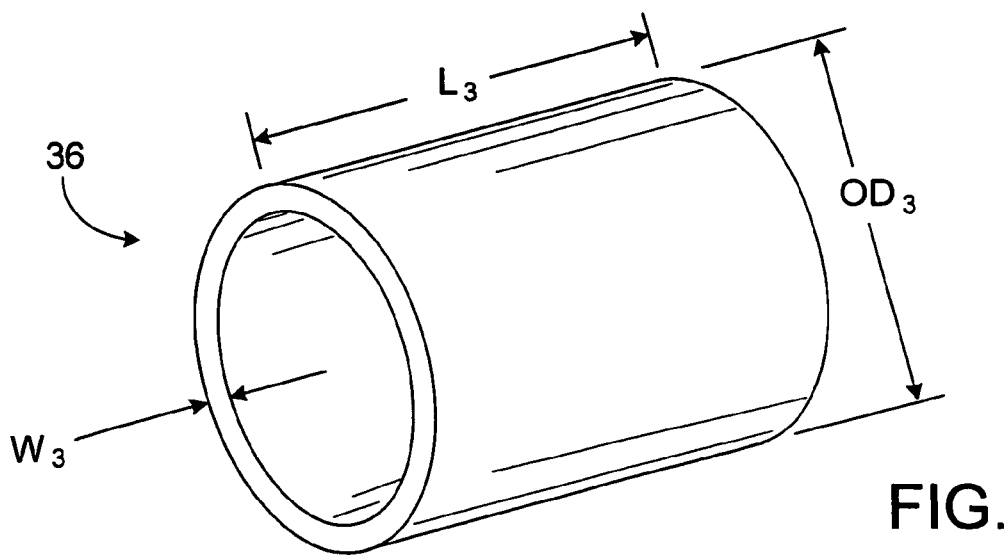
FIG. 3 is a perspective view of the endoprosthesis shown in FIG. 1 in a second expanded position.

In a specific embodiment, endoprosthesis 10 can be fashioned from a polymer composition having a hard segment (H'), a first soft segment ($S''_1$), and a second soft segment ($S''_2$). The first soft segment ($S''_1$) has a $T_{trans}$ at least 10° C. lower than $T_{trans}$ of the hard segment (H'), and at least 10° C. above $T_{trans}$ of the second soft segment ($S''_2$). The composition is shaped, e.g., extruded or molded, into the form of the second expanded position 36 (FIG. 3) at a temperature above $T_{trans}$ of the hard segment (H'). Cooling the endoprosthesis to a temperature below that of $T_{trans}$ of the first soft segment ($S''_1$), but above that of the second soft segment ($S''_2$), enables shaping, e.g., by compression, into the form of the first expanded position 32 (FIG. 2). Cooling below $T_{trans}$ of the second soft segment ($S''_2$) enables shaping the endoprosthesis into the form of collapsed position 30 (FIG. 1). Now, heating the endoprosthesis above $T_{trans}$ of the second soft segment ($S''_2$) reverts the collapsed position 30 (FIG. 1) to the first expanded position 32 (FIG. 2). Heating the endoprosthesis in the first expanded position 32 above $T_{trans}$ of the first soft segment ($S''_1$) expands the endoprosthesis from the first expanded position 32 to the second expanded position 36 (FIG. 3). Finally, heating above $T_{trans}$ of the hard segment (H') causes the endoprosthesis to lose all shapes in memory.

Suitable polymers can have an elastic modulus of about 60,000 or 70,000 psi or more at 25° C. (ASTM D638M), e.g., from about 100,000 to about 250,000 or more, e.g., from about 250,000 to about 500,000 or more, e.g., from about 500,000 to about 1,000,000 or more.

The polymers can be thermoplastic, thermoset, crystalline or amorphous. The polymers or portions of the polymers, e.g., a polymer segment or block, can be degradable, natural, or synthetic.

Natural polymers or polymer portions include, for example, zein, casein, gelatin, gluten, serum albumin, collagen, polysaccharides, polyhyaluronic acid, poly(3-hydroxyalkanoate)s, alginate, dextran, cellulose and collagen. Synthetic polymers or polymer portions include, for example, chemical derivatives of collagen, chemical derivatives of cellulose, polyphosphazenes, poly(vinyl alcohols), polyamides, polyacrylates, polyalkylenes, polyacrylamides, polyalkylene glycols, polyalkylene terephthalates, polyvinyl ethers, polyvinyl esters and polyvinyl halides, polyvinylpyrrolidone, polyesters. Degradable polymers or polymer portions include, for example, polyester amides, polyanhydrides, polycarbonates, polyorthoesters, polylactides, polyglycolides, polysiloxanes, polyurethanes and cellulose derivatives.

Generally, any of the above polymers can be cross-linked during their polymerization, or after their polymerization in a secondary step. The polymers can be cross-linked by application of radiation such as e-beam, UV, gamma, x-ray radiation or by heat-activated chemical crosslinking techniques, utilizing azo compounds or peroxides, e.g., organic peroxides, e.g., benzoyl peroxide. Radiation techniques provide the advantage that the polymer typically does not have to be substantially heated to achieve crosslinking. For e-beam radiation, an exposure of about 200-300, e.g. 250 kilograys, typically provides sufficient crosslinking.

Tubular endoprosthesis 10 can include a coating, e.g., a polymeric coating applied to an exterior surface of endoprosthesis 10, that includes a therapeutic agent. In some embodiments, the polymeric material from which endoprosthesis 10 is made includes a therapeutic agent dispersed therein. The therapeutic agent can, for example, prevent restenosis. In a specific embodiment, the medicament is paclitaxel.

In general, a therapeutic agent can be a genetic therapeutic agent, a non-genetic therapeutic agent, or cells. Therapeutic agents can be used singularly, or in combination. Therapeutic agents can be, for example, nonionic, or they may be anionic and/or cationic in nature.

Exemplary non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, and (r) hormones.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

In addition to therapeutic agents, any of the polymers mentioned may be filled with a non-therapeutic agent, for example, nanoparticles of clay and silica to, for example, increase the modulus of the plastic. Dispersing agents and/or compatibilizing agents may be used, for example, to improve the blending of polymers and the blending of polymers with fillers. Dispersing agents and/or compatibilizing agents include, for example, ACRAWAX® (ethylene bis-stearamide), polyurethanes and ELVALOY® (acrylic-functionalized polyethylene).

In specific embodiments, the filler is a radio-opaque agent, e.g., bismuth carbonate or barium sulfate. In other specific embodiments, the polymeric material includes a thermal conductor, e.g., a boron nitride.

Endoprosthesis 10 can be bio-absorbable or non-bioabsorbable, and can be used in, e.g., a vascular or a non-vascular lumen or cavity. Examples of non-vascular lumens include the esophagus, the prostate, a ureteral lumen or a lumen in the biliary system.

Referring back now to FIGS. 1-3, endoprosthesis 10 can be of any desired size. Depending on the application, endoprosthesis 10 in collapsed position (FIG. 1) can, e.g., have a length $L_1$ from about 3 mm and about 75 mm, an outer diameter $OD_1$ from about 1 mm to about 20 mm, and a wall thickness $W_1$ of from about 1 mm to about 5 mm. Depending on the application, endoprosthesis 10 in first expanded position 32 can, e.g., have a length $L_2$ of from about 0.6 $L_1$ to about 0.95 $L_1$, an outer diameter $OD_2$ from about 1.2 $OD_1$ to about 30 $D_1$, and a wall thickness $W_2$ from about 0.5 $W_1$ to about 0.9 $W_1$. After further expansion, endoprosthesis 10 in second expanded position 36 can, e.g., have a have a length $L_3$ of from about 0.6

$L_2$ to about 0.95 $L_2$, an outer diameter $OD_3$ from about 1.2 $OD_2$ to about 3 $OD_2$, and a wall thickness $W_3$ from about 0.5 $W_2$ to about 0.9 $W_2$.

In specific embodiments, a coronary endoprosthesis can, e.g., have a first expanded diameter of from about 2 mm to about 6 mm, a peripheral endoprosthesis can, e.g., have a first expanded diameter of from about 5 mm to about 24 mm and a gastrointestinal and/or urological endoprosthesis can, e.g., have a first expanded diameter of from about 6 mm to about 30 mm. In other specific embodiments, a neurological endoprosthesis can, e.g., have a first expanded diameter of from about 1 mm to about 12 mm, an abdominal aortic aneurysm (AAA) endoprosthesis or a thoracic aortic aneurysm (TAA) endoprosthesis can, e.g., have a first expanded diameter of from about 20 mm to about 46 mm, and a renal endoprosthesis can, e.g., have a first expanded diameter of from about 8 mm to about 12 mm.

When it is desirable, endoprosthesis 10 can be configured for reduced foreshortening. For example, endoprosthesis 10 in collapsed position 30 can have a collapsed transverse dimension $OD_1$ and a collapsed longitudinal length $L_1$, such that after heating above the first temperature and expansion to the first expanded position 32, that is at least about fifty percent larger than the collapsed transverse dimension, a first expanded longitudinal length $L_2$, decreases by less than about fifty percent, measured relative to the collapsed longitudinal length. In addition, after heating above the second temperature and expansion to the second expanded position 36 having a second expanded transverse dimension $OD_3$ that is at least about twenty-five percent larger than the first expanded transverse dimension $OD_2$, a second expanded longitudinal length $L_3$, measured at the second expanded position, decreases by less than about twenty-five percent, measured relative to the first expanded longitudinal length.

Figure 9A:
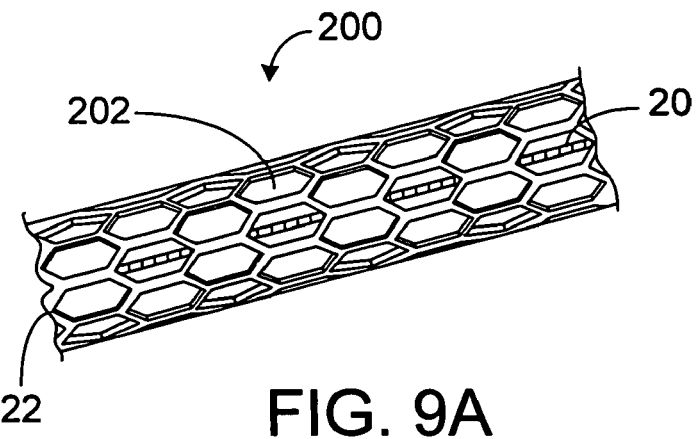
FIGS. 9A and 9B are perspective views of apertured endoprostheses.
Figure 9B:
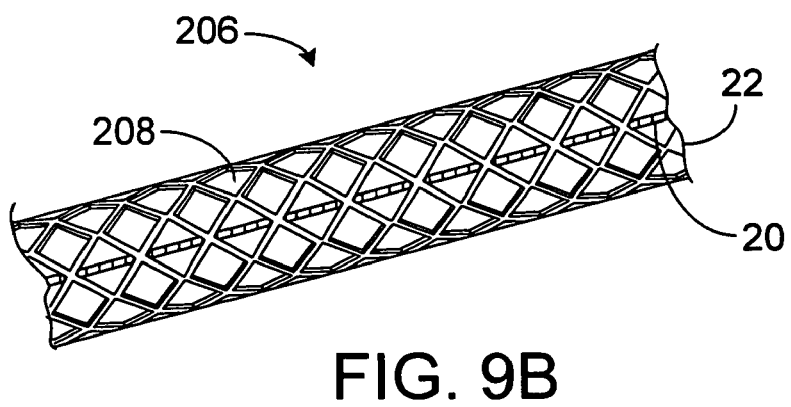

Referring now to FIGS. 9A and 9B, each tubular endoprosthesis 200, 206 includes longitudinal elements 20 embedded in wall 22, and each endoprosthesis 200, 206 has a collapsed position that can be reverted to a first expanded position larger than the collapsed position by heating to a first temperature subsequent to insertion of the endoprosthesis into a cavity or lumen, and that can be further expanded to a second expanded position larger than the first expanded position within the cavity or lumen by heating to a second temperature higher than the first temperature. In addition, each endoprosthesis 200, 206 includes a plurality of apertures 202, 208 defined in wall 22. As shown, endoprosthesis 200 has apertures 202 that are hexagonal in shape, and endoprosthesis 206 has apertures 208 that are square in shape. Also, in each embodiment 200, 206 each longitudinal element is disposed longitudinally across some of the apertures 202, 208 such that the longitudinal element effectively bifurcates some of the apertures. The embodiments of FIGS. 9A and 9B exhibit reduced foreshortening during expansion for two reasons. First, as described above, we have discovered that embedding a longitudinal element generally reduces endoprosthesis foreshortening during expansion. In addition, apertures reduce foreshortening because during expansion, the apertures defined in the wall of the endoprosthesis can be stretched. Having longitudinal elements bifurcating some of the apertures allows the polymeric material of the endoprosthesis to "fill-in" around the wire during compression. In addition, this arrangement provides for increased strength and prevents tissue from growing through the apertures.

The endoprosthesis described herein can be formed by a variety of techniques known in the art. For example, some embodiments are desirably formed by extrusion or co-extrusion, while other embodiments are desirably formed by molding, e.g., injection molding, co-molding, compression molding, or casting. For molded embodiments, longitudinal elements are embedded in a wall by placing the elements on a mold insert. Apertures can be formed by laser ablation or by forming the apertures in the wall of the endoprosthesis as the endoprosthesis is molded.

A number of embodiments of the invention have been described. Nevertheless, it will be understood that various modifications may be made without departing from the spirit and scope of the invention.

For example, while in some embodiments tubular endoprosthesis 10 has a transverse cross-section that is circular, in some embodiments its transverse cross-section is non-circular. For example, it can be elliptical or polygonal, e.g., square, pentagonal, hexagonal or octagonal.

While FIGS. 9A and 9B show hexagonal and square apertures, wall 22 can include an aperture of other shapes, e.g., circular or elliptical. Other polygonal shapes are also possible, including pentagonal and octagonal.

While in some embodiments, the collapsed position is substantially an entire longitudinal length of the endoprosthesis, in other embodiments, only a portion of the endoprosthesis is in a collapsed position, e.g., 10 percent, 20 percent or 40 percent of the overall length of the endoprosthesis.

Figure 10A:
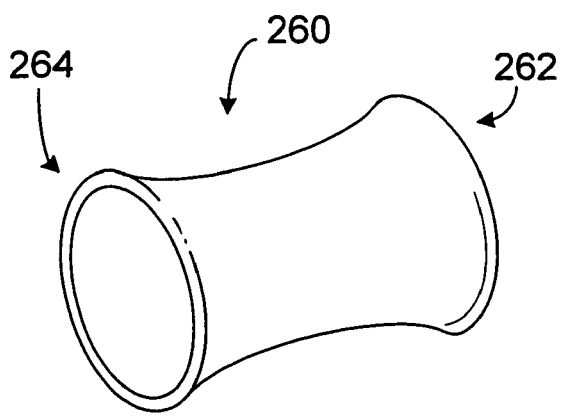
FIG. 10A is a perspective view of an alternative endoprosthesis with two end portions in expanded positions.

While in some embodiments, the expanded position is substantially an entire longitudinal length of the endoprosthesis, in other embodiments, only a portion of the endoprosthesis is in an expanded position. Referring to FIG. 10A, an endoprosthesis 260 has been expanded from a collapsed position so that only end portions 262 and 264 are in an expanded position.

Figure 10B:
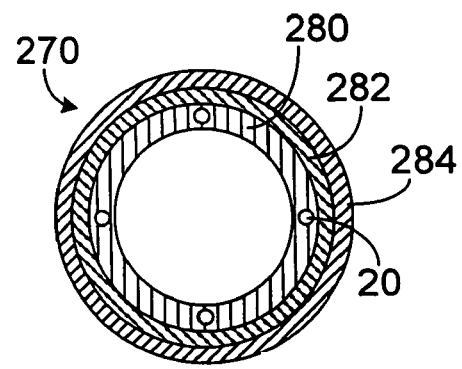
FIG. 10B is a cross-sectional view of an alternative endoprosthesis having a three-layer wall.

While in some embodiments the wall of the tubular endoprosthesis includes only a single layer, in some embodiments, the wall includes more than one layer, e.g., 2, 3, 5 or 7 layers. For example, referring to FIG. 10B, an endoprosthesis 270 is shown that includes a wall that includes three layers 280, 282 and 284. Longitudinal element 20 is embedded in layer 280 of wall 22. Each layer may be made of the same material or each layer may be made of a different material.

Figure 11:
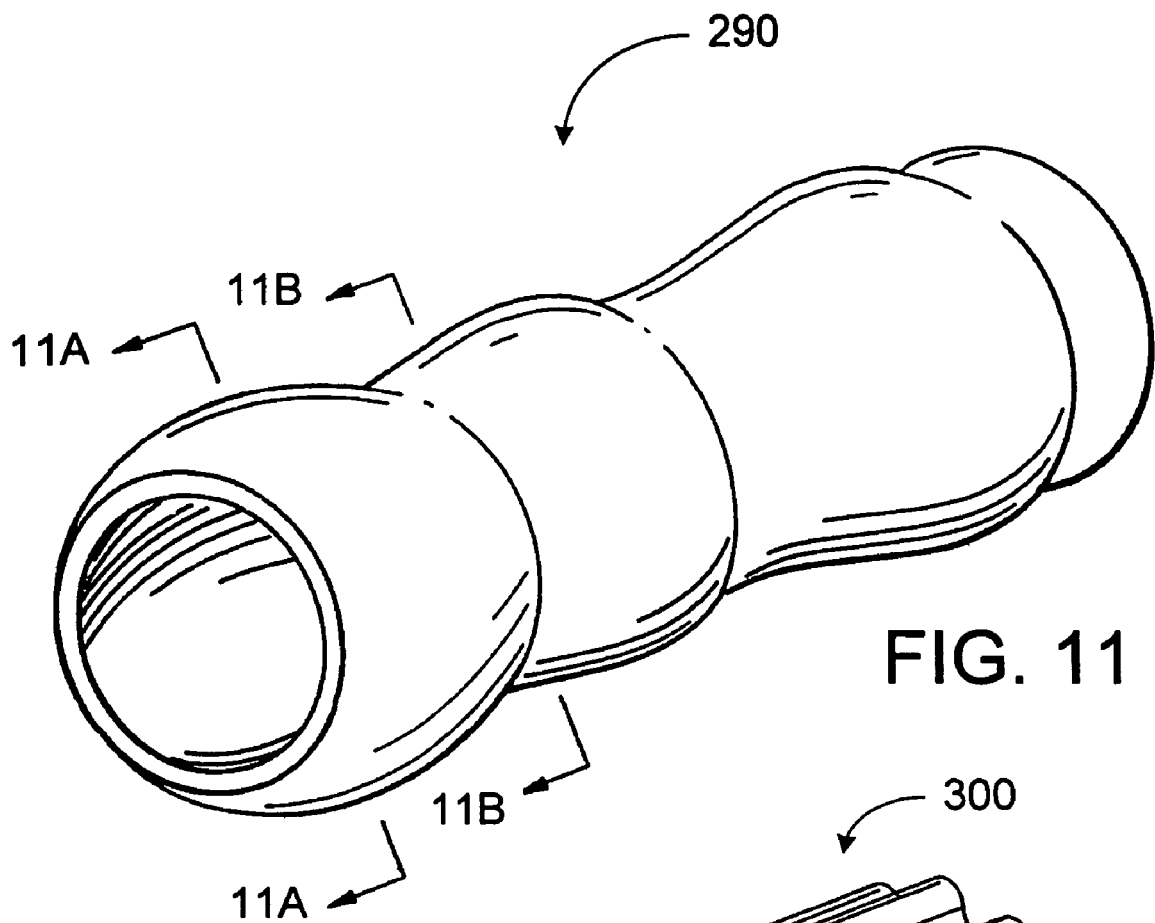
FIG. 11 is a perspective view of an alternative endoprosthesis having different wall thicknesses along its longitudinal length.
Figure 11A:
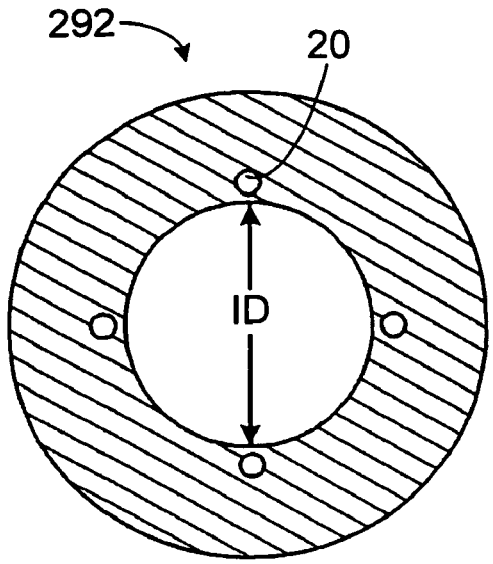
FIGS. 11A and 11B are cross-sectional views of the endoprosthesis shown in FIG. 11, taken along 11A-11A or 11B-11B, respectively.
Figure 11B:
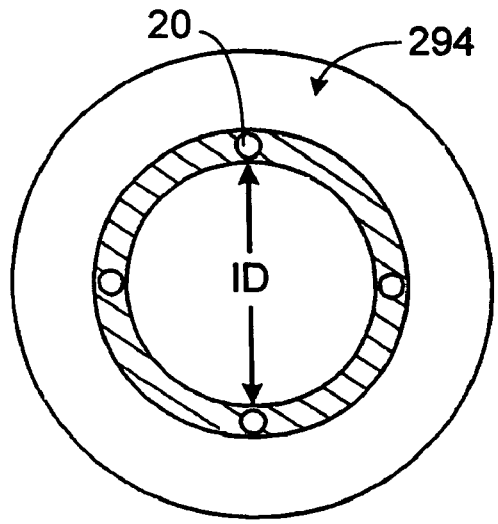

While some endoprotheses have been shown that have a longitudinally constant wall thickness, in some embodiments, the wall thickness is longitudinally non-constant. In addition, while some endoprotheses have been shown that have a constant outer diameter, in some embodiments the outer diameter is non-constant. Referring to FIGS. 11, 11A and 11B, a tubular endoprosthesis 290 has a constant inner diameter ID, but a non-constant outer diameter. The outer diameter is varied by varying wall thickness of the endoprosthesis as shown in FIGS. 11A and 11B. As shown, section 292 has a thicker wall than section 294. Varying the wall thickness improves lateral flexibility which enables the endoprosthesis, e.g., to be used in lumens and cavities with high curvature.

Figure 12:
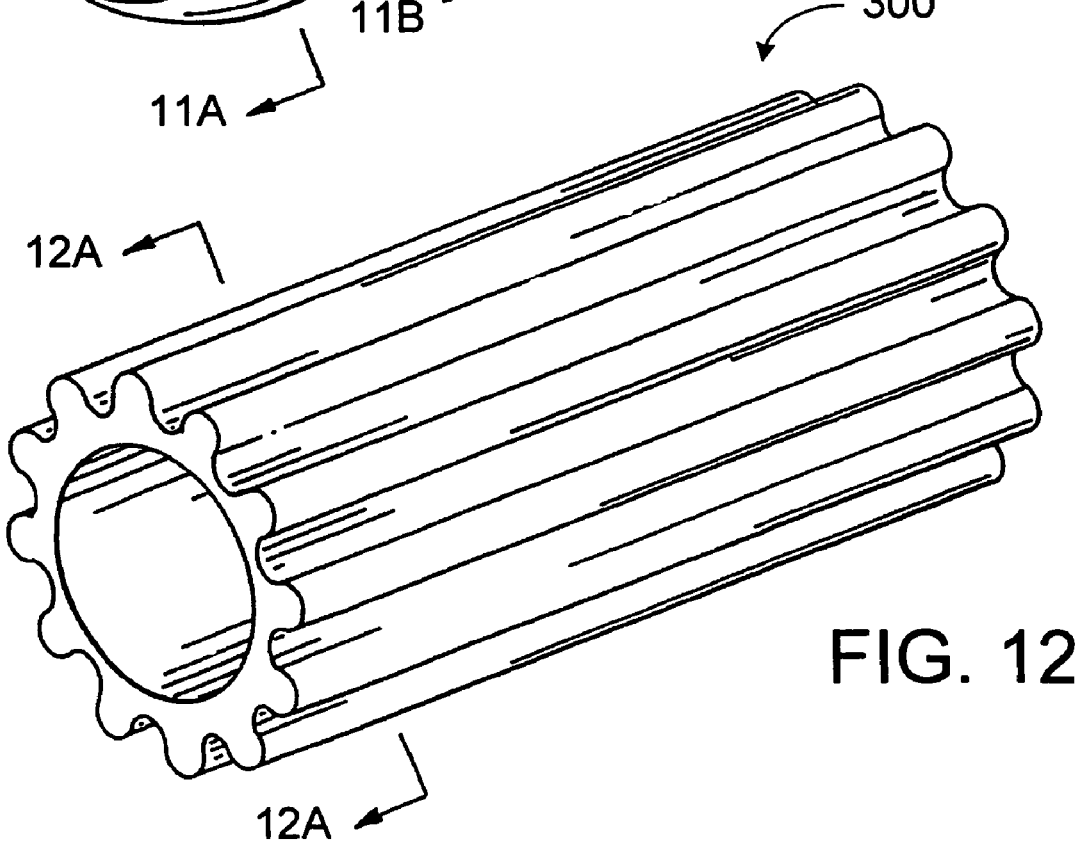
FIG. 12 is a perspective view of an alternative endoprosthesis having longitudinal ribs.
Figure 12A:
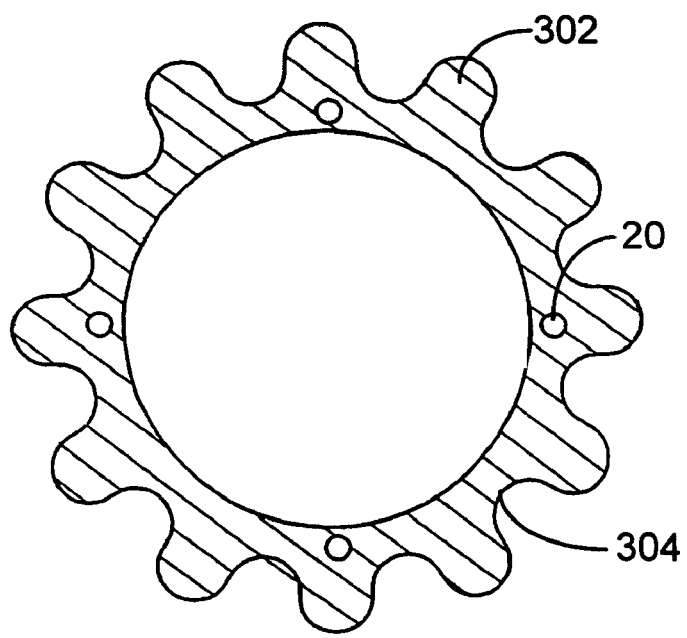
FIG. 12A is a cross-sectional view of the endoprosthesis shown in FIG. 12, taken along 12A-12A.

While some endoprotheses have been shown that have a transversely constant wall thickness, in some embodiments, the wall thickness is transversely non-constant. Referring to FIGS. 12 and 12A, endoprosthesis 300 includes a wall that is in the shape of a sprocket in transverse cross-section. The wall has thick areas 302 and thin areas 304 that extend longitudinally along a length of endoprosthesis 300. This type of endoprosthesis reduces lateral flexibility and increases strength when that is desirable.

A number of embodiments of have been described. Still other embodiments are within the scope of the following claims.

What is claimed is:

1. A tubular endoprosthesis comprising a shape memory polymeric material, the endoprosthesis having at least one longitudinal element, a wall of the endoprosthesis surrounding at least a portion of the at least one longitudinal element, the endoprosthesis having a collapsed position that can be reverted to a first expanded position larger than the collapsed position by heating the wall to a first temperature subsequent to insertion of the endoprosthesis into a cavity or lumen in a mammal, wherein the endoprosthesis can be further expanded from the first expanded position to a second expanded position within the cavity or lumen in the mammal by heating the wall to a second temperature which is higher than the first temperature, said polymeric material comprising a hard segment, a first soft segment having a first transition temperature, and a second soft segment having a second transition temperature, wherein heating the endoprosthesis above the first transition temperature reverts the collapsed position to the first expanded position and wherein heating the endoprosthesis in the first expanded position above the second transition temperature expands the endoprosthesis from the first expanded position to the second expanded position.

2. The tubular endoprosthesis of claim 1, wherein the endoprosthesis is substantially circular in transverse cross-section.

3. The tubular endoprosthesis of claim 1, wherein the longitudinal element comprises a metal.

4. The tubular endoprosthesis of claim 3, wherein the metal comprises stainless steel.

5. The tubular endoprosthesis of claim 1, wherein the longitudinal element is a monofilament.

6. The tubular endoprosthesis of claim 5, wherein the monofilament is circular in transverse cross-section, having a diameter of from about 0.0005 inch to about 0.010 inch.

7. The tubular endoprosthesis of claim 1, wherein the longitudinal element is a multifilament.

8. The tubular endoprosthesis of claim 1, wherein the endoprosthesis includes from two to twelve longitudinal elements.

9. The tubular endoprosthesis of claim 1, wherein the longitudinal element extends substantially along an entire longitudinal length of the endoprosthesis.

10. The tubular endoprosthesis of claim 1, wherein the wall includes at least one aperture.

11. The tubular endoprosthesis of claim 10, wherein the aperture is circular in transverse cross-section.

12. The tubular endoprosthesis of claim 10, wherein the longitudinal element is disposed longitudinally across the aperture.

13. The tubular endoprosthesis of claim 1, wherein the tubular endoprosthesis includes a coating comprising a therapeutic agent.

14. The tubular endoprosthesis of claim 13, wherein the coating is on an outer surface of the endoprosthesis.

15. The tubular endoprosthesis of claim 13, wherein the coating is an outer surface of the endoprosthesis, and wherein the therapeutic agent also is dispersed generally throughout the polymeric material.

16. The tubular endoprosthesis of claim 13, wherein the therapeutic agent prevents restenosis.

17. The tubular endoprosthesis of claim 13, wherein the therapeutic agent is paclitaxel.

18. The tubular endoprosthesis of claim 1, wherein the polymeric material includes a radio-opaque agent.

19. The tubular endoprosthesis of claim 1, wherein the polymeric material includes a thermal conductor.

20. The tubular endoprosthesis of claim 19, wherein the thermal conductor is a boron nitride.

21. The tubular endoprosthesis of claim 1, wherein the polymeric material comprises a polymer that is selected from the group consisting of natural polymers, zein, casein, gelatin, gluten, serum albumin, collagen, polysaccharides, polyhyaluronic acid, poly(3-hydroxyalkanoate)s, alginate, dextran, cellulose, collagen, synthetic polymers, chemical derivatives of collagen, chemical derivatives of cellulose, polyphosphazenes, poly(vinyl alcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyesters, degradable polymers, polyester amides, polyanhydrides, polycarbonates, polyorthoesters, polylactides, polyglycolides, polysiloxanes, polyurethanes, cellulose derivatives, and mixtures thereof 22. The tubular endoprosthesis of claim 1, wherein the endoprosthesis has a collapsed transverse dimension and a collapsed longitudinal length, both measured at the collapsed position, and wherein the first expanded position has a first expanded transverse dimension that is at least fifty percent larger than the collapsed transverse dimension and a first expanded longitudinal length that is at least fifty percent of the collapsed longitudinal length.

23. The tubular endoprosthesis of claim 1, wherein the endoprosthesis has a first expanded transverse dimension and a first expanded longitudinal length, both measured at the first expanded position, and wherein the second expanded position has a second expanded transverse dimension that is at least twenty-five percent larger than the first expanded transverse dimension and a second expanded longitudinal length that is at least fifty percent of the first expanded longitudinal length.

24. A method of treating a cavity or lumen in a mammal, the method comprising:
  inserting, into the cavity or lumen in the mammal, a tubular endoprosthesis in accordance with claim 1; and
  heating the inserted endoprosthesis to the first temperature to revert the collapsed position to the first expanded position.

25. The method of claim 24, further comprising heating the inserted endoprosthesis to the second temperature to further expand the endoprosthesis to the second expanded position.

26. The method of claim 24, wherein the heating is performed with a liquid.

27. The method of claim 24, wherein the first temperature is from about 37° C. to about 55° C.

28. The method of claim 24, wherein the second temperature is from about 40° C. to about 75° C.

29. The method of claim 24, wherein the heating is performed by a delivery tube that includes a warmed liquid.

30. The method of claim 29, wherein the delivery tube is a balloon catheter.

31. The method of claim 24, wherein the lumen a vascular lumen.

32. The tubular endoprosthesis of claim 1, wherein the polymeric material is a shape memory polymer having a shape memory in the collapsed, the first expanded position and the second expanded position.

33. The endoprosthesis of claim 1, wherein the at least one longitudinal element is substantially straight along an entire length of the endoprosthesis.

34. The endoprosthesis of claim 1, wherein the wall of the endoprosthesis defines a plurality of apertures therein and the longitudinal element bifurcates at least one of the apertures.

35. The endoprosthesis of claim 1, wherein the second transition temperature is at least 10° C. below a transition temperature of the hard segment and at least 10° C. above the first transition temperature.

36. The endoprosthesis of claim 1, wherein the at least one longitudinal element is configured to reduce endoprosthesis foreshortening as the endoprosthesis expands from the collapsed position to the first expanded position and from the first expanded position to the second expanded position.

37. An endoprosthesis comprising a shape memory polymeric material and at least one longitudinal element configured to reduce endoprosthesis foreshortening as the endoprosthesis expands from a collapsed position to an expanded position, the wall of the endoprosthesis surrounding at least a portion of the at least one longitudinal element, said polymeric material comprising a hard segment, a first soft segment having a first transition temperature, and a second soft segment having a second transition temperature, wherein heating the endoprosthesis above the first transition temperature reverts the collapsed position to the first expanded position and wherein heating the endoprosthesis in the first expanded position above the second transition temperature expands the endoprosthesis from the first expanded position to the second expanded position.

38. The endoprosthesis of claim 37, wherein the endoprosthesis includes from about two to twelve longitudinal elements.

39. A method of treating a cavity or lumen in a mammal, the method comprising:
  inserting, into the cavity or lumen in the mammal, a tubular endoprosthesis in accordance with claim 32;
  heating the inserted endoprosthesis to the first temperature to revert the collapsed position to the first expanded position; and then
  heating the inserted endoprosthesis to the second temperature to further expand the endoprosthesis to the second expanded position.

40. The endoprosthesis of claim 37, wherein the at least one longitudinal element is substantially straight along an entire length of the endoprosthesis.

41. The endoprosthesis of claim 37, wherein the wall of the endoprosthesis defines a plurality of apertures therein and the longitudinal element bifurcates at least one of the apertures.

42. The endoprosthesis of claim 37, wherein the second transition temperature is at least 10° C. below a transition temperature of the hard segment and at least 10° C. above the first transition temperature.

* * * * *

UNITED STATES PATENT AND TRADEMARK OFFICE
CERTIFICATE OF CORRECTION

| | | |
|---|---|---|
| PATENT NO. | : 8,043,361 B2 | Page 1 of 1 |
| APPLICATION NO. | : 11/010129 | |
| DATED | : October 25, 2011 | |
| INVENTOR(S) | : Paul Dicarlo and Ilya Yampolsky | |

It is certified that error appears in the above-identified patent and that said Letters Patent is hereby corrected as shown below:

Col. 12, line 52, after "lumen" add "is".

Signed and Sealed this
Seventeenth Day of January, 2012

David J. Kappos
*Director of the United States Patent and Trademark Office*